(12) United States Patent
Vresilovic et al.

(10) Patent No.: US 8,287,595 B2
(45) Date of Patent: Oct. 16, 2012

(54) HYDROGEL BALLOON PROSTHESIS FOR NUCLEUS PULPOSUS

(75) Inventors: Edward Vresilovic, Ardmore, PA (US); Michele S. Marcolongo, Aston, PA (US); Anthony M. Lowman, Wallingford, PA (US); Alastair J. T. Clemow, Princeton, NJ (US); Michael F. Keane, Downington, PA (US)

(73) Assignee: Synthes USA, LLC, West Chester, PA (US)

( * ) Notice: Subject to any disclaimer, the term of this patent is extended or adjusted under 35 U.S.C. 154(b) by 1007 days.

(21) Appl. No.: 11/510,747

(22) Filed: Aug. 25, 2006

(65) Prior Publication Data
US 2007/0073402 A1   Mar. 29, 2007

Related U.S. Application Data

(60) Provisional application No. 60/711,430, filed on Aug. 26, 2005.

(51) Int. Cl.
*A61F 2/44* (2006.01)
(52) U.S. Cl. ............... 623/17.12; 623/17.11; 623/17.16; 606/279
(58) Field of Classification Search .... 623/17.11–17.16; 606/61, 194, 279
See application file for complete search history.

(56) References Cited

U.S. PATENT DOCUMENTS

| | | | |
|---|---|---|---|
| 5,047,055 A | 9/1991 | Bao et al. | |
| 5,192,326 A | 3/1993 | Bao et al. | |
| 5,260,066 A | 11/1993 | Wood et al. | |
| 5,288,503 A | 2/1994 | Wood et al. | |
| 5,534,028 A | 7/1996 | Bao et al. | |
| 5,863,551 A | 1/1999 | Woerly | |
| 5,976,186 A | 11/1999 | Bao et al. | |
| 5,981,826 A | 11/1999 | Ku et al. | |
| 6,280,475 B1 * | 8/2001 | Bao et al. | 623/17.16 |
| 6,932,843 B2 * | 8/2005 | Smith et al. | 623/17.11 |

(Continued)

FOREIGN PATENT DOCUMENTS

JP   09-313593   12/1997

(Continued)

OTHER PUBLICATIONS

PCT International Search Report, issued on Oct. 22, 2007, for PCT Application No. PCT/US2006/033276.

(Continued)

*Primary Examiner* — Alvin Stewart
*Assistant Examiner* — Julianna N Harvey
(74) *Attorney, Agent, or Firm* — Stradley Ronon Stevens & Young, LLP

(57) ABSTRACT

A prosthesis for replacing or supplementing a nucleus pulposus of an intervertebral disk is an expandable container having flexible walls, the container being adapted to be inserted into a central cavity of an intervertebral disk through a narrow cannula, and the flexible walls are made from a biocompatible hydrogel. A preferred hydrogel is a cryogel formed from an aqueous solution of poly(vinyl alcohol) and poly(vinyl pyrrolidone). The prosthesis may be prepared by dip-coating a mandrel with an aqueous solution of a hydrogel-forming polymer or mixture of such polymers, gelling the coated solution by chilling, and subjecting the gelled coating to a series of repeated freeze-thaw treatments. In use, the prosthesis is inserted into a central cavity of an intervertebral disk and filled with biocompatible material, e.g., a biocompatible liquid, a biocompatible polymer, and a biocompatible hydrogel, particularly a thermogelling hydrogel.

18 Claims, 4 Drawing Sheets

U.S. PATENT DOCUMENTS

| | | | |
|---|---|---|---|
| 2003/0033017 A1 | 2/2003 | Lotz | |
| 2003/0134032 A1* | 7/2003 | Chaouk et al. | 427/2.24 |
| 2004/0029994 A1* | 2/2004 | Cheng et al. | 523/113 |
| 2004/0078090 A1* | 4/2004 | Binette et al. | 623/23.76 |
| 2004/0091540 A1* | 5/2004 | Desrosiers et al. | 424/486 |
| 2004/0186471 A1* | 9/2004 | Trieu | 606/61 |
| 2004/0220296 A1 | 11/2004 | Lowman et al. | |
| 2005/0055099 A1* | 3/2005 | Ku | 623/17.16 |
| 2006/0009844 A1* | 1/2006 | Bloemer et al. | 623/17.11 |
| 2006/0177468 A1* | 8/2006 | Katsikis et al. | 424/209.1 |
| 2006/0206209 A1* | 9/2006 | Cragg et al. | 623/17.16 |
| 2006/0241768 A1* | 10/2006 | Trieu | 623/17.12 |
| 2006/0293561 A1* | 12/2006 | Abay, II | 600/104 |

FOREIGN PATENT DOCUMENTS

| | | |
|---|---|---|
| JP | 2003-038637 | 2/2003 |
| JP | 2003513685 | 4/2003 |
| JP | 200407318 | 3/2004 |
| WO | WO 98/55053 | 12/1998 |
| WO | WO 01/32100 A2 * | 5/2001 |
| WO | WO 02/085262 A1 | 10/2002 |
| WO | WO 03/020169 A2 | 3/2003 |
| WO | WO 2004/028414 A1 | 4/2004 |
| WO | WO 2004/052248 A1 | 6/2004 |
| WO | WO 2004052248 | 6/2004 |
| WO | WO 2004009875 | 11/2004 |
| WO | WO 2005023150 | 3/2005 |
| WO | WO 2005/032358 A2 | 4/2005 |
| WO | WO 2005/113032 A2 | 12/2005 |
| WO | WO 2006/105190 A2 | 10/2006 |

OTHER PUBLICATIONS

PCT International Preliminary Report on Patentability, issued Feb. 26, 2008, for PCT Application No. PCT/US2006/033276.

Thomas, Jonathan, "The Effect of Dehydration History on PVA/PVP Hydrogels for Nucleus Pulposus Replacement", Journal of Biomedical Materials Research, Wiley, New York, NY, US, vol. 69, No. 2, May 15, 2004, pp. 135-140.

JP Office Action dated May 13, 2011 (w/English Translation).

* cited by examiner

HYDROGEL BALLOON PROSTHESIS FOR NUCLEUS PULPOSUS

CROSS REFERENCE TO RELATED APPLICATION

This application claims priority under 35 U.S.C. §119(e) to U.S. Provisional Application No. 60/711,430, filed Aug. 26, 2005, which is incorporated by reference herein in its entirety.

1. FIELD OF THE INVENTION

The present invention relates to methods and apparatus for replacing or supplementing the natural nucleus pulposus of the intervertebral disc, and more particularly to an expandable or inflatable balloon prosthesis made from a hydrogel for replacing or supplementing the nucleus pulposus.

2. BACKGROUND OF THE INVENTION

Chronic back pain, typically lower back pain, caused by injury or age-related degeneration of an intervertebral disc is a condition experienced by many patients.

Current treatment options for lower back pain range from conservative bed rest to highly invasive surgical procedures, including spinal fusion, discectomy, and total disc replacement.

The human intervertebral disc is comprised of two major structures, an inner gelatinous structure (i.e., the nucleus pulposus) and an outer tendinous structure (i.e., the annulus fibrosus). Degeneration of the nucleus can lead to disc degradation and loss of function. Thus, another surgical option for the relief of lower back pain is replacement of the nucleus while leaving the annulus intact.

Replacement or supplementation of the nucleus pulposus, e.g., by introducing a biocompatible material, which may be a liquid, a gel, or the like, can relieve pain, restore healthy physiologic function to the disc, and/or prevent additional wear on the annulus.

Accordingly, a need has continued to exist for a method and apparatus that make it possible to confine an injected or otherwise introduced material, e.g., a gel or liquid, within the nucleus pulposus region of the intervertebral disk.

3. SUMMARY OF THE INVENTION

The invention of this application addresses the many problems relating to confinement of gels, liquids, or the like, introduced into the region of the nucleus pulposus.

According to the invention, a hollow expandable or inflatable vessel made from a hydrogel is inserted into the nucleus pulposus region of an intervertebral disk, optionally after a portion or the entirety of the natural nucleus pulposus has been removed, and the vessel is then expanded by introducing a gel, liquid, or the like, to provide an intradiscal structure that supplements or replaces the natural nucleus pulposus.

Accordingly, one aspect of the invention is to provide a structure for replacing or supplementing the natural nucleus pulposus of an intervertebral disc.

A further aspect is to provide a structure that can confine an injected liquid but which can also expand and deform to completely fill a cavity within an intervertebral disk.

A further aspect is to provide an expandable structure, such as a balloon, that is made of a biocompatible polymer.

A further aspect is to provide an expandable structure, such as a balloon, that is made of a hydrogel containing poly(vinyl alcohol) or a mixture of associating polymers containing poly(vinyl alcohol).

A further aspect is to provide an expandable structure, such as a balloon, that is made of a hydrogel containing poly(vinyl alcohol), or a mixture of associating polymers containing poly(vinyl alcohol), that can be formed by a process of dip-coating a mandrel.

A further aspect is to provide an expandable structure, such as a balloon, that is made of a hydrogel containing poly(vinyl alcohol) or a mixture of associating polymers containing poly(vinyl alcohol).

A further aspect is to provide a method for replacing or supplementing a nucleus pulposus of an intervertebral disk by inserting a flexible-walled container or balloon made from a hydrogel into the nucleus pulposus region of the intervertebral disk by a minimally invasive surgical procedure and subsequently expanding the container or balloon by introducing a material having properties appropriate for replacing or supplementing a natural nucleus pulposus.

Further aspects of the invention will be apparent from the description of the invention which follows.

4. BRIEF DESCRIPTION OF THE DRAWINGS

5. DETAILED DESCRIPTION OF THE INVENTION

Figure 1:
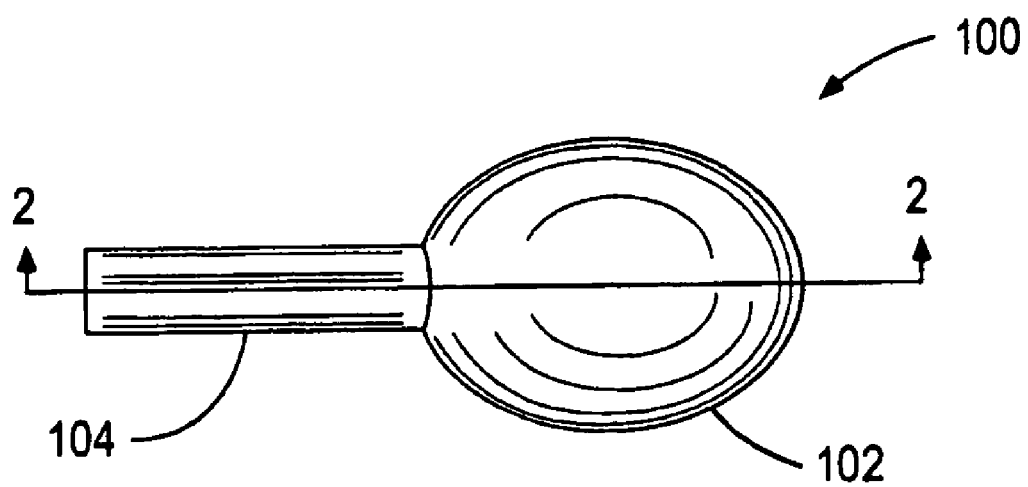
FIG. 1 shows an expandable hollow prosthesis of one embodiment of the invention.

As the intervertebral disc ages, the nucleus pulposus may experience certain pathological conditions. Normal aging causes the water content of the nucleus to decrease, resulting in a reduced ability to support the loads imposed on it and a reduction in the height of the intervertebral disc. As a result of degeneration of the annulus fibrosus, a portion of the nucleus may become herniated through cracks in the annulus and cause pain by impinging upon the spinal nerve roots. Accordingly, at least the herniated portion of the nucleus may be removed surgically to alleviate the pain. In some conditions the entire nucleus pulposus may be surgically removed. Such surgery may be effective to relieve pain, but may leave the intervertebral disc without an adequately functioning nucleus pulposus, thus leaving the possibility of further degeneration of the intervertebral disc. Accordingly, it may be desirable to supplement a degenerated nucleus pulposus or to replace an excised portion or even the entire nucleus in order to restore at least some of the functionality provided by the intact, undegenerated nucleus pulposus.

According to one embodiment of the invention, a prosthesis for replacing or supplementing the nucleus pulposus of an intervertebral disk comprises an expandable balloon made from a hydrogel material, whereby the wall of the balloon is comprised of a hydrogel. In certain embodiments, the wall of the balloon may have a thickness from 0.01 to 2.00, more preferably, from 0.02 mm to 1.00 mm. In certain other embodiments, the balloon may have a tensile modulus of 0.02 MPa to 0.8 MPa at 30% strain. In certain other embodiments, the wall of the balloon may have a thickness from 0.01 to 2.00, more preferably, from 0.02 mm to 1.00 mm, and the balloon may have a tensile modulus of 0.02 MPa to 0.8 MPa at 30% strain. Preferably, the balloon is capable of having a volume expansion of 3 to 5 times the original volume before bursting.

The balloon is collapsible, e.g., by folding, rolling, or the like, to a relatively small size preferably for insertion into the central cavity of the intervertebral disk through a minimally invasive opening, optionally after a portion or substantially all of the nucleus pulposus has been removed. To this end, the wall of the balloon is made as a flexible membrane having a thickness and strength sufficient to support the internal pressure exerted by a filling material. In use, the balloon prosthesis is collapsed to a relatively small volume and inserted into the central cavity of the intervertebral disc, e.g., through a cannula inserted through the annulus fibrosus or through a channel made in the body of an adjacent vertebra. Thus, the balloon prosthesis is typically inserted by a conventional minimally invasive surgical technique.

Once the balloon has been implanted in the nucleus pulposus cavity, it is expanded by insertion of a relatively incompressible material into its interior in order to supplement or replace the nucleus pulposus. The balloon may deform as it is expanded to substantially completely fill the available volume within the space left by the degeneration and/or surgical removal of the body of the nucleus pulposus. Alternatively, the balloon may be originally made in a shape to conform to a cavity left by such degeneration or surgical removal. The filling of the balloon is preferably continued until it has substantially filled the available volume within the nucleus pulposus cavity and has been pressurized to substantially restore the natural pressure within the nucleus pulposus region of the intervertebral disk. Preferably the balloon is expanded within the nucleus pulposus region to the extent that the natural disk height for a given individual patient is restored.

The hydrogel material that forms the wall of the balloon prosthesis may include any biocompatible hydrogel that has sufficient strength to confine the filling material under pressures existing within the region of the nucleus pulposus. Suitable hydrogels may be selected from among the many known hydrogels, including those disclosed, e.g., in U.S. Pat. No. 5,047,055, to Bao et al., the entire disclosure of which is incorporated herein by reference. A preferred material for forming the balloon prosthesis is a hydrogel based on poly(vinyl alcohol) (PVA) that can be formed by repeated freeze-thaw cycles of an aqueous solution of PVA as described, e.g., in U.S. Pat. Nos. 5,260,066 and 5,288,503, to Wood et al., and U.S. Pat. No. 5,981,826, to Ku et al., the entire disclosures of which are incorporated herein by reference. Such materials, generally referred to as cryogels, are solid materials having elastomeric properties containing a large proportion, e.g., over 80%, of water, which are produced when solutions of relatively high molecular weight PVA of a high degree of hydrolysis are subjected to repeated freeze-thaw cycles. Such cryogels are tough, elastomeric, resilient, substantially insoluble in water below about 50° C., and nontoxic. A particularly preferred material is a cryogel formed by repeated freeze-thaw cycles of an aqueous solution of a mixture of PVA with another associating polymer such as poly(vinyl pyrrolidone) (PVP). Accordingly, the preferred embodiments of the cryogel may comprise a blend of PVA and 0.1% to 50%, more preferably 1% to 5% of a second polymer, preferably PVP or copolymers of PVP and poly(methyl methacrylate), poly(acrylamide), poly(acrylic acid), poly(acrylonitrile), or poly(ethylene glycol). The polymer component of such hydrogels may comprise from about 0.5% by weight to about 25% by weight of PVP, the remainder being PVA. In preferred hydrogels of this type the polymer component may incorporate from about 0.5% to about 5% by weight of PVP, for example, about 2.5% of PVP, the remainder being PVA. Such hydrogels are disclosed in U.S. patent application Ser. No. 10/111,782, to Marcolongo et al. (European Patent No. EP 1 229 873), the entire disclosure of which is incorporated herein by reference.

Figure 2:
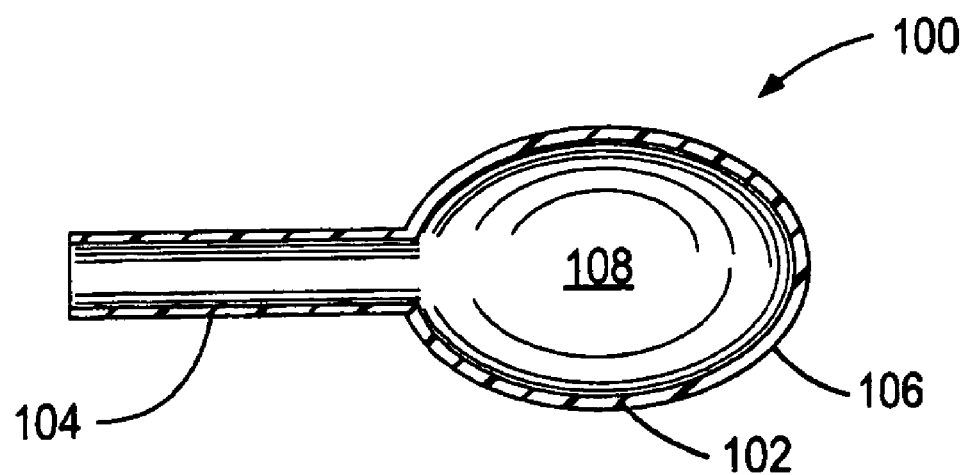
FIG. 2 shows a cross-section of the prosthesis of FIG. 1 taken along the line 2-2 in FIG. 1.

The expandable balloon prosthesis may be made in any shape that is suitable for filling the cavity of the nucleus pulposus of an intervertebral disk. FIG. 1 shows a prosthesis 100 having a generally ellipsoidal chamber 102 and a filling tube 104 through which the prosthesis is filled with a relatively incompressible material after implantation. FIG. 2 shows a cross-section of the prosthesis of FIG. 1 along the line 2-2 in FIG. 1, showing the thin membrane wall 106 surrounding an interior volume 108. Such a prosthesis may be prepared from a hydrogel that has sufficient elasticity to allow the balloon to deform under the internal pressure of the filling material to substantially fill void space within the nucleus pulposus region of the intervertebral disc.

Figure 3:
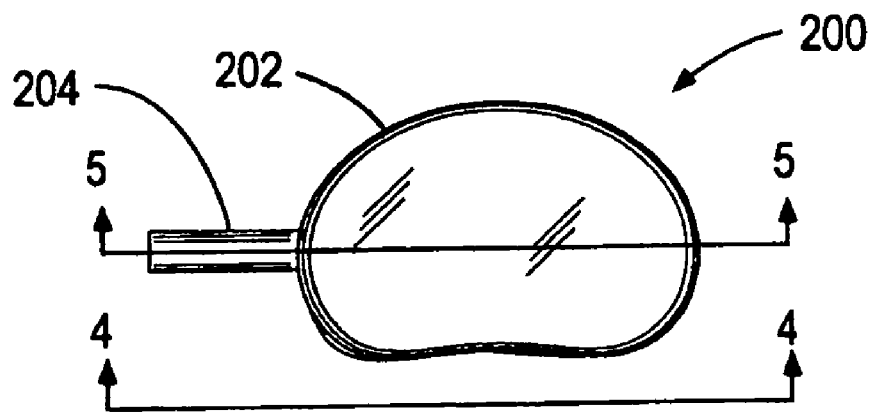
FIG. 3 shows a plan view of another embodiment of the prosthesis of one embodiment of the invention wherein the expandable container is molded generally in the shape of a natural nucleus pulposus.
Figure 4:
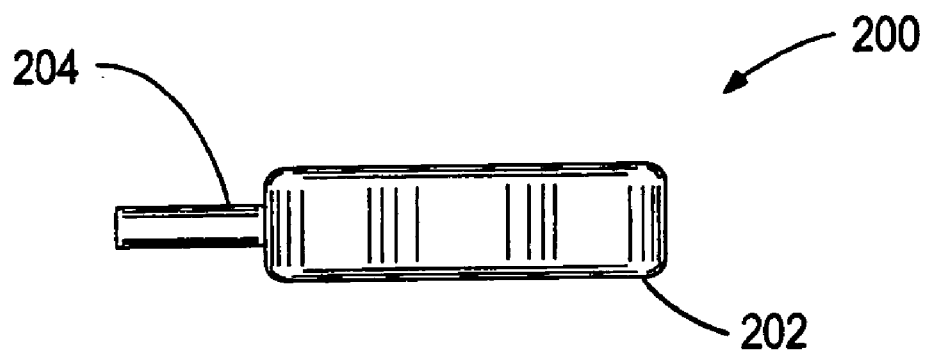
FIG. 4 shows an elevation view of the prosthesis of FIG. 3 in the direction indicated by the arrows 4-4 in FIG. 3.
Figure 5:
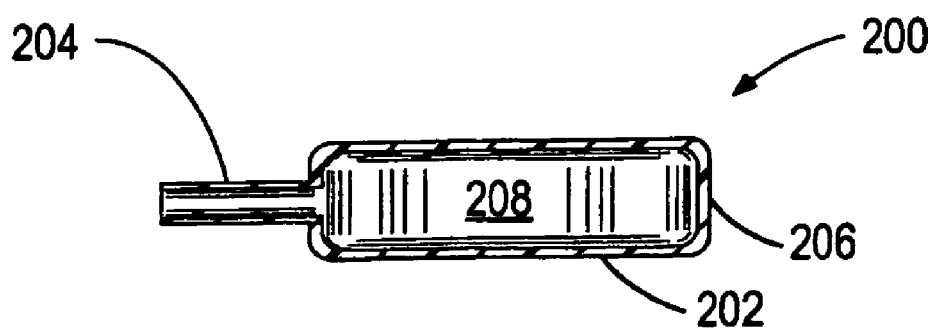
FIG. 5 shows a cross-section of the prosthesis of FIGS. 3 and 4 taken along the line 5-5 in FIG. 3.

FIG. 3 shows a plan view of another prosthesis 200 wherein the inflatable chamber 202 of the prosthesis 200 has been molded in the general shape of the natural nucleus pulposus. The prosthesis 200 is also provided with a filling tube 204. FIG. 4 shows an elevational view of the prosthesis of FIG. 3 in the direction indicated by the arrows 4-4 in FIG. 3. FIG. 5 shows a cross-sectional view of the prosthesis 200 of FIG. 3 taken along the line 5-5 in FIG. 3. FIG. 5 shows the membrane wall 206 and internal volume 208 of the prosthesis.

The balloon prosthesis may be manufactured by any conventional process for forming a hollow container having a flexible membrane wall. The container may be formed by conventional methods for forming objects from synthetic polymers such as blow molding, injection molding, rotational molding, extrusion, and the like. The container may also be formed by adhesive assembly of thin, flexible sheets of a hydrogel. It is preferred to form the balloon by dip-coating a mandrel with a dispersion or solution of a polymer capable of forming a cryogel in a suitable liquid vehicle, e.g., water, subsequently solidifying the coating on the mandrel by drying, chilling, or the like, and then subjecting the balloon to repeated freeze-thaw cycles to form a cryogel balloon. A particularly preferred method of forming the hydrogel balloon is by dip-coating a mandrel with an aqueous dispersion of a PVA or PVA-PVP blend followed by rapid chilling to a temperature that is effective to cause the coated layer to form a gel. Such a temperature will typically be below −20° C. Rapid chilling of the coating of polymer dispersion on the mandrel can be accomplished by dipping the coated mandrel into liquid nitrogen having a temperature of about −198.5° C. (77.35 K). The hydrogel coating so formed may then be further processed by several cycles of freezing and thawing, as is conventional for such hydrogels. The balloon is then removed from the mandrel and is ready for use in the process of the invention.

Figure 6:
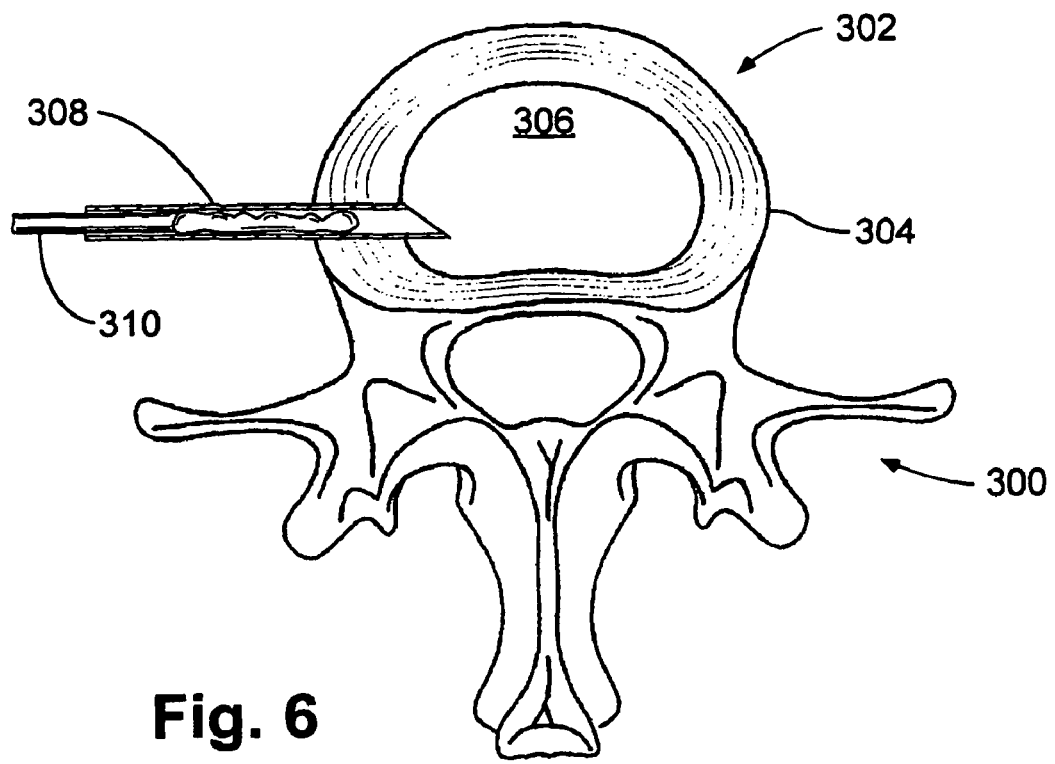
FIG. 6 shows a schematic cross-section of a spinal motion segment showing a tubular insertion instrument with a prosthesis of one embodiment of the invention in collapsed form mounted on a filling tube within the insertion tube.
Figure 7:
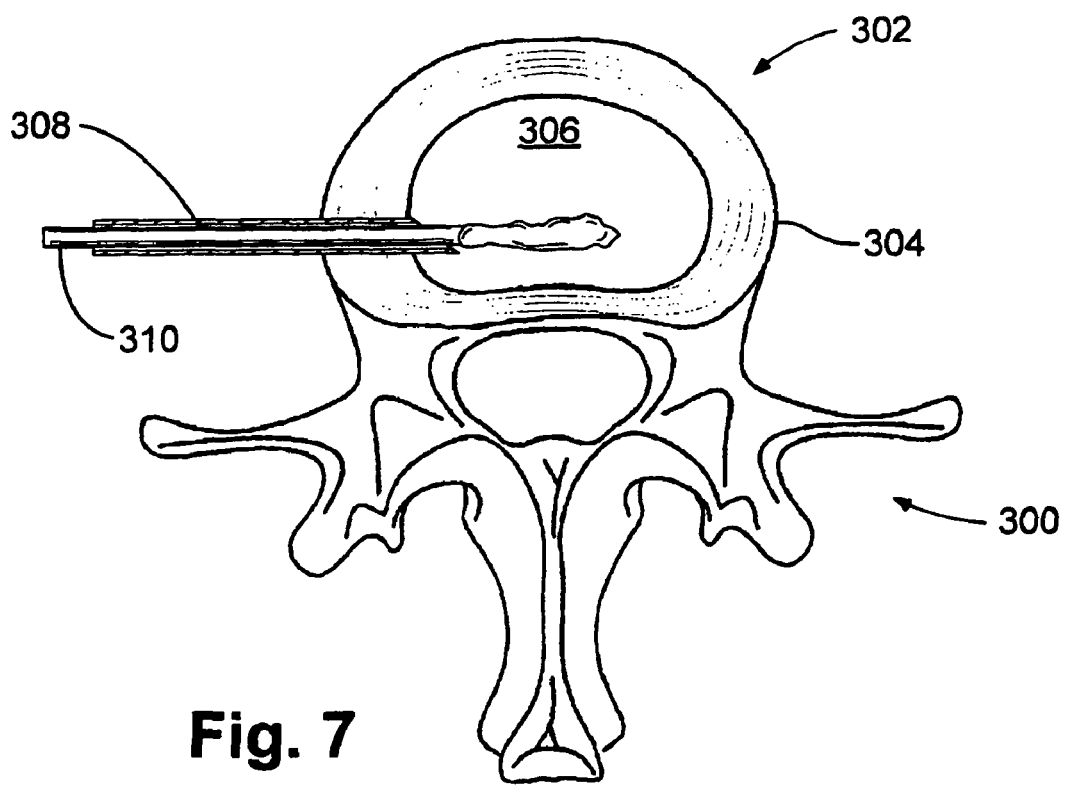
FIG. 7 shows the prosthesis in collapsed form inserted into the nucleus pulposus cavity of an intervertebral disk, optionally after removal of all or part of the natural nucleus pulposus.
Figure 8:
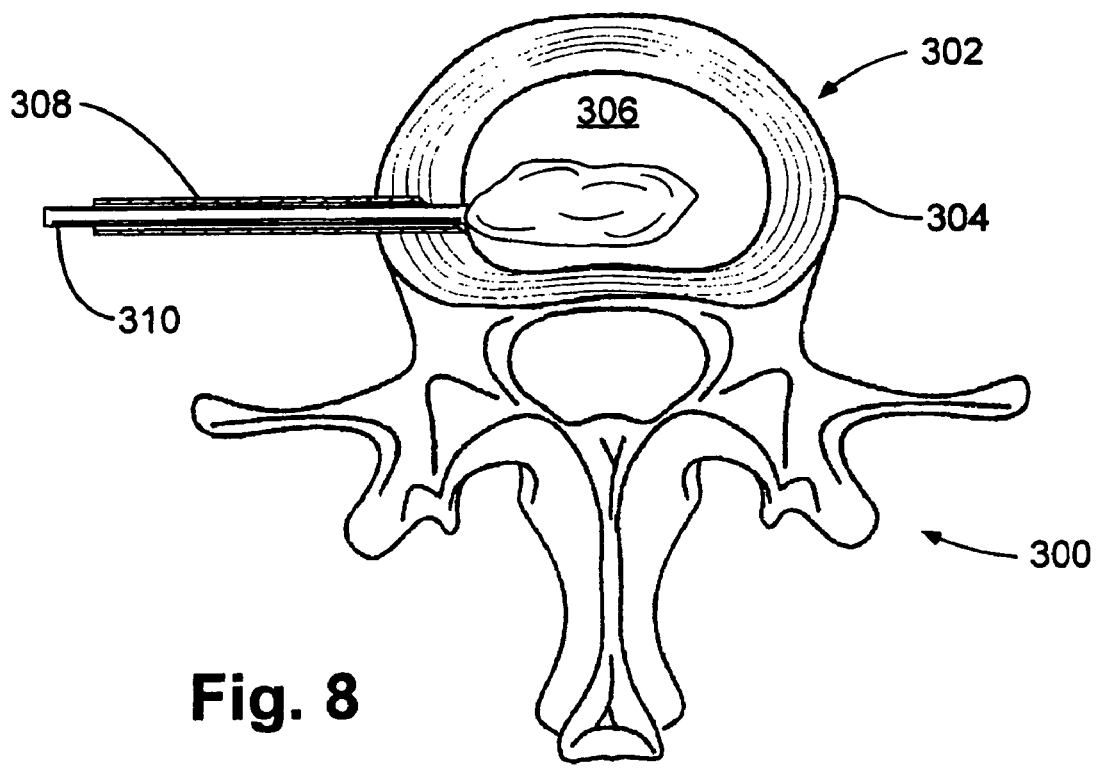
FIG. 8 shows the prosthesis being expanded within the intervertebral disk by insertion of a filler material through the filling tube.
Figure 9:
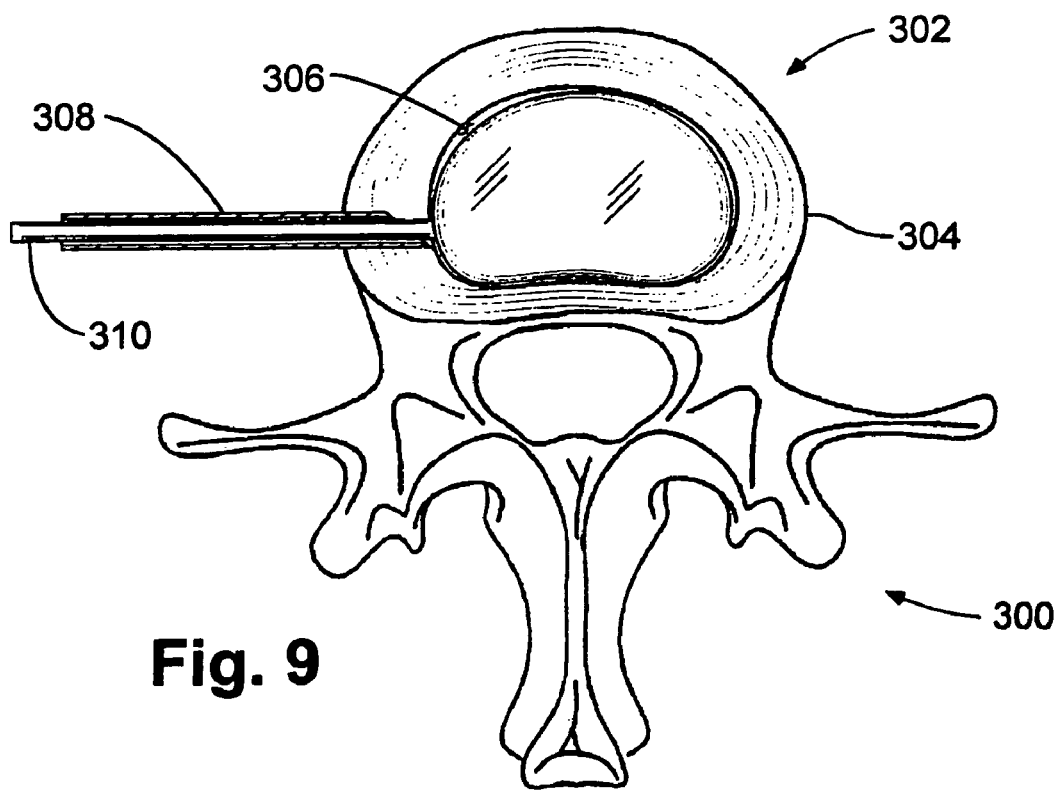
FIG. 9 shows the prosthesis fully expanded within the intervertebral disk and sealed.

The implantation and filling of a hydrogel balloon prosthesis is schematically illustrated in FIGS. 6-9. The figures illustrate schematically a superior or cranial view of a typical lumbar vertebra 300 with intervertebral disc 302 having an annulus fibrosus 304 and a central volume 306 representing a void space due to degeneration of the nucleus pulposus or removal thereof by a surgical procedure. An insertion cannula or trocar 308 is inserted through the annulus fibrosus 304 and into the central volume 306. A balloon prosthesis 100 is collapsed, as by folding or rolling, attached to a carrier tube 310, and introduced into the insertion tube 308. FIG. 6 shows the balloon prosthesis 100 within the insertion tube 308, just before implantation. FIG. 7 shows the initial stage of the implantation wherein the balloon prosthesis 100 has been positioned within the central volume 306 of the annulus fibrosus 304 by advancing the carrier tube 310 through the insertion tube 308. FIG. 8 shows an intermediate stage in the implantation wherein the balloon prosthesis 100 has been partially inflated with material introduced through the carrier tube 310. FIG. 9 shows the final stage of the implantation wherein the balloon prosthesis 100 has been completely inflated and substantially fills the central volume 306 of the annulus fibrosus 304. After the inflation of the balloon prosthesis 100 is complete, the fill tube is sealed by any conventional procedure, e.g., by insertion of a plug, tying off, etc., the carrier tube 310 is detached and withdrawn, and the insertion tube is withdrawn from the annulus fibrosus.

The balloon prosthesis 100 may be inflated with any material that will remain confined by the hydrogel membrane of the balloon prosthesis and will provide mechanical properties similar to those of the natural nucleus pulposus. Thus, the balloon prosthesis may be filled with a curable material injected in a liquid or plastic state that will cure after injection to an elastic or viscoelastic material preferably having properties similar to those of the natural nucleus pulposus.

A preferred material for filling the balloon prosthesis of the invention is a hydrogel that can be injected in a liquid or soft injectable state and that will preferably provide the prosthesis with mechanical properties similar to those of the natural nucleus pulposus. A particularly preferred material is a thermogelling composition that can be injected in a liquid form at a temperature approximating room temperature and that will then become converted to a gel form when it is heated to normal body temperature. Such compositions are known, and include, for example, thermogelling hydrogel materials based on poly(N-isopropylacrylamide) (PNIPAAm) or a copolymer or blend of PNIPAAm, as disclosed in U.S. Published Patent Application No. 2004/0220296 (application Ser. No. 10/837,082), by Lowman et al., the entire disclosure of which is incorporated herein by reference. After the balloon prosthesis has been implanted, such a thermogelling composition may be injected into the balloon at a relatively low temperature at which it remains a flowable liquid, e.g., about 20° C. to about 27° C. After injection, the thermogelling hydrogel is warmed, typically merely by conduction of heat from its surroundings, to body temperature of about 37° C. and forms a solid hydrogel. The solid hydrogel so formed will not flow out through the neck of the balloon; accordingly no special sealing of the input stem or neck of the balloon is needed in this embodiment.

Typical thermogelling hydrogels based on PNIPAAm are disclosed in U.S. Published Patent Application No. 2004/0220296, and include those prepared from blends of aqueous solutions of PNIPAAm with aqueous solutions of poly(vinyl alcohol) (PVA), and aqueous solutions of poly(ethylene glycols) (PEGs) of various molecular weights. Also disclosed are thermogelling hydrogels prepared from aqueous solutions of PNIPAAm-grafted PEG polymers and aqueous solutions of PEG-PNIPAAm-PEG triblock polymers. Such thermogelling hydrogels, and the like, are preferred materials for filling the balloon prosthesis.

Alternatively, the balloon prosthesis can be filled with a conventional biocompatible liquid. After the injection of such a liquid, the neck of the balloon is sealed by conventional procedures, e.g., sealing with a plug, sealing with an adhesive, heat-sealing, stitching, or the like.

The balloon prosthesis may also be filled or packed with a solid hydrogel in the form of beads or a string that will serve to provide the prosthesis with the requisite mechanical properties. Depending on the cross-section of the inserted material, the neck or stem of the balloon may be sealed as indicated above. If the size, shape, stiffness, or other properties of the inserted solid hydrogel material are such that it will not be extruded through the neck of the balloon, special sealing of the stem need not be performed.

The invention having now been described in terms of certain preferred embodiments, it will be understood that modifications and changes can be made thereto without departing from the spirit and character thereof.

What is claimed:

1. A prosthesis for replacing or supplementing a nucleus pulposus of an intervertebral disk, comprising a pre-formed expandable balloon having flexible walls defining an inner cavity, the flexible walls having a thickness from about 0.02 mm to about 1.00 mm and a filling tube passing through the flexible walls and in communication with the inner cavity so that the prosthesis is fillable, said pre-formed balloon being adapted to be inserted into the intervertebral disk through a cannula, wherein said flexible walls are made from a material comprising a cryogel formed from subjecting an aqueous solution comprising poly (vinyl alcohol) to repeated freeze-thaw cycles, said expandable pre-formed balloon being filled through the filling tube with a biocompatible material selected from the group consisting of a biocompatible liquid, a biocompatible polymer, and a biocompatible hydrogel in an expanded configuration, and the prosthesis having a tensile modulus of about 0.02 MPa to about 0.8 MPa at 30% strain.

2. The prosthesis of claim 1, wherein said cryogel is formed from an aqueous solution further comprising poly (vinyl pyrrolidone).

3. The prosthesis of claim 1, having a shape in the expanded configuration generally conforming to the shape of a natural nucleus pulposus.

4. The prosthesis of claim 1, wherein said biocompatible hydrogel is a thermogelling hydrogel.

5. The prosthesis of claim 4, wherein said thermogelling hydrogel is prepared from a mixture of a first aqueous solution comprising poly (N-isopropylacrylamide) and a second aqueous solution comprising poly (vinyl alcohol).

6. The prosthesis of claim 4, wherein said thermogelling hydrogel is prepared from a mixture of a first aqueous solution comprising poly (N-isopropylacrylamide) and a second aqueous solution comprising poly (ethylene glycol).

7. The prosthesis of claim 4, wherein said thermogelling hydrogel is prepared from an aqueous solution comprising a poly (N-isopropylacrylamide)-grafted poly (ethylene glycol) polymer.

8. The prosthesis of claim 4, wherein said thermogelling hydrogel is prepared from an aqueous solution comprising a poly (ethylene glycol)-poly (N-isopropylacrylamide)-poly (ethylene glycol) triblock polymer.

9. The prosthesis of claim 4, wherein said thermogelling hydrogel is prepared from a mixture of a first aqueous solution comprising poly (vinyl alcohol) and a second aqueous solution comprising poly (ethylene glycol).

10. A method of replacing or supplementing a nucleus pulposus of an intervertebral disk, comprising the steps of:
(i) providing a pre-formed flexible-walled balloon having an inner cavity, flexible walls defining the inner cavity, the flexbile walls having a thickness from about 0.02 mm to about 1.00 mm and a filling tube passing through the flexible walls and in communication with the inner cavity so that the prosthesis is fillable, the flexible walls made from a cryogel formed from subjecting an aqueous solution comprising poly (vinyl alcohol) to repeated freeze-thaw cycles,
(ii) inserting the pre-formed flexible-walled balloon into the intervertebral disk by a minimally invasive surgical procedure in a collapsed configuration, and
(iii) introducing into said inner cavity through said filling tube of said pre-formed flexible-walled balloon a biocompatible material selected from the group consisting of a biocompatible liquid, a biocompatible polymer, and a biocompatible hydrogel for expanding said pre-formed balloon into an expanded configuration to replace or supplement the nucleus pulposus, the filled balloon in the expanded configuration having a tensile modulus of about 0.02 MPa to about 0.8 MPa at 30% strain.

11. The method of claim 10, wherein said cryogel is formed from an aqueous solution further comprising poly (vinyl pyrrolidone).

12. The method of claim 10, wherein said pre-formed flexible-walled balloon has a shape in the expanded configuration generally conforming to the shape of a nucleus pulposus.

13. The method of claim 10, wherein said biocompatible hydrogel is a thermogelling hydrogel.

14. The method of claim 13, wherein said thermogelling hydrogel is prepared from a mixture of a first aqueous solution comprising poly (N-isopropylacrylamide) and a second aqueous solution comprising poly (vinyl alcohol).

15. The method of claim 13, wherein said thermogelling hydrogel is prepared from a mixture of an aqueous solution comprising a poly (N-isopropylacrylamide) and a second aqueous solution comprising poly (ethylene glycol).

16. The method of claim 13, wherein said thermogelling hydrogel is prepared from an aqueous solution comprising a poly (N-isopropylacrylamide)-grafted poly (ethylene glycol) polymer.

17. The method of claim 13, wherein said thermogelling hydrogel is prepared from an aqueous solution comprising a poly (ethylene glycol)-poly (N-isopropylacrylamide)-poly-(ethylene glycol) triblock polymer.

18. The method of claim 13, wherein said thermogelling hydrogel is prepared from a mixture of a first aqueous solution comprising poly (vinyl alcohol) and a second aqueous solution comprising poly (ethylene glycol).

* * * * *

UNITED STATES PATENT AND TRADEMARK OFFICE
CERTIFICATE OF CORRECTION

| | | |
|---|---|---|
| PATENT NO. | : 8,287,595 B2 | |
| APPLICATION NO. | : 11/510747 | |
| DATED | : October 16, 2012 | |
| INVENTOR(S) | : Edward Vresilovic et al. | |

It is certified that error appears in the above-identified patent and that said Letters Patent is hereby corrected as shown below:

On the Title Page Item (73) should read:

(73) Assignee: Synthes USA, LLC, West Chester, PA (US)
Drexel University, Philadelphia, PA (US)

Signed and Sealed this
Twenty-eighth Day of May, 2013

Teresa Stanek Rea
*Acting Director of the United States Patent and Trademark Office*